United States Patent
Lee et al.

(10) Patent No.: US 6,991,858 B2
(45) Date of Patent: Jan. 31, 2006

(54) BLUE LIGHT-EMITTING COMPOUND FOR ORGANIC ELECTROLUMINESCENT DEVICE AND ORGANIC ELECTROLUMINESCENT DEVICE USING THE SAME

(75) Inventors: Kwan Hee Lee, Seoul (KR); Soo Jin Park, Seoul (KR); Jong In Hong, Seoul (KR); Kyung Sun Choi, Seoul (KR); Chan Hyo Lee, Seoul (KR); Dae Yup Shin, Suwon (KR); Dong Hyun Jung, Suwon (KR); Sang Hyun Ju, Seoul (KR); Jang Hyuk Kwon, Suwon (KR)

(73) Assignee: Samsung SDI Co., Ltd., Suwon (KR)

( * ) Notice: Subject to any disclaimer, the term of this patent is extended or adjusted under 35 U.S.C. 154(b) by 0 days.

(21) Appl. No.: 10/359,003

(22) Filed: Feb. 4, 2003

(65) Prior Publication Data

US 2004/0001971 A1 Jan. 1, 2004

(30) Foreign Application Priority Data

Jun. 20, 2002 (KR) ........................ 2002-34691

(51) Int. Cl.
*H05B 33/14* (2006.01)
*C09K 11/06* (2006.01)
*C07D 471/00* (2006.01)

(52) U.S. Cl. ............... 428/690; 428/917; 313/504; 313/506; 257/102; 252/301.16; 546/81; 546/110; 546/122; 546/183

(58) Field of Classification Search .......... 428/690, 428/917; 313/504, 506; 257/102; 252/301.16; 546/81, 110, 122, 183
See application file for complete search history.

(56) References Cited

U.S. PATENT DOCUMENTS 4,235,911 A * 11/1980 Sarges ............... 514/278
6,224,966 B1    5/2001 Sakai et al. ........... 428/212

FOREIGN PATENT DOCUMENTS

EP  0 388 768 B1  8/1995
JP  10-261488     9/1998

OTHER PUBLICATIONS

Ferrarini et al., "Synthesis and beta–blocking activity of (R,S)–(E)–oximeethers of 2,3–dihydro–1,8–naphthyridine . . . Part IX", Eur. J. Med. Chem. 35 (2000), pp. 815–826, no month.*
C.W. Tang, et al., "Organic electroluminescent diodes" Appl. Phys. Lett. 51 (12), Sep. 21, 1987, pp 913–915.
Tetsuo Tsutsui, et al., "Significance of multilayer structures in organic thin–film electroluminescent devices" SPIE vol. 1910, pp 180–189, 1993, no month.

* cited by examiner

*Primary Examiner*—Marie Yamnitzky
(74) *Attorney, Agent, or Firm*—Christie, Parker & Hale, LLP

(57) ABSTRACT

The present invention relates to a blue light-emitting compound for organic polymer EL devices and organic EL devices having superior color purity and light-emitting efficiency by providing a blue light-emitting compound for organic EL devices represented by Chemical Formula 1 and an organic EL device using the blue light-emitting compound:

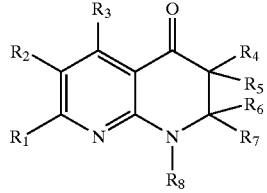

Chemical Formula 1 wherein $R_1$ to $R_8$ each independently represents a functional group selected from the group consisting of hydrogen alkyl groups, alkoxy groups, carbon rings, aryl groups, hetero rings and fused aromatic compounds having from 1 to 30 carbon atoms; to of $R_1$ to $R_3$ may additionally be connected by a ring; and two of $R_4$ to $R_8$ may additionally be connected by a ring.

10 Claims, 3 Drawing Sheets

BLUE LIGHT-EMITTING COMPOUND FOR ORGANIC ELECTROLUMINESCENT DEVICE AND ORGANIC ELECTROLUMINESCENT DEVICE USING THE SAME

CROSS REFERENCE TO RELATED APPLICATIONS

This application claims priority of Korea Patent Application No. 2002-34691 filed on Jun. 20, 2002 in the Korean Intellectual Property Office, the disclosure of which is incorporated herein by reference.

FIELD OF THE INVENTION

The present invention relates to a blue light-emitting compound for an organic electroluminescent device and an organic electroluminescent device using the same, and more particularly, to a blue light-emitting compound useful in an organic electroluminescent device that is an emissive display device, and that has a wide viewing angle, superior contrast and a fast response time, and an organic electroluminescent device using the blue light-emitting compound.

BACKGROUND OF THE INVENTION

An electroluminescent (hereinafter referred to as "EL") device has the advantages of a wide viewing angle, superior contrast, and a fast response time as an emissive display device.

EL devices are categorized as inorganic EL devices and organic EL devices according to materials for forming a light-emitting layer, wherein the organic EL has merits of superior luminescence, driving voltage and response speed characteristics as well as multi-coloration.

Existing EL devices generally consist of an anode electrode for injecting a hole, a hole injecting layer for injecting and transporting the hole, a hole transport layer, a light-emitting layer, an electron transport layer and a cathode electrode.

In an organic EL device illustrated in FIG. 1, a hole extends from an anode electrode 12 formed on a substrate 11 to a light-emitting layer 15 through a hole injection layer 13 and a hole transport layer 14, and electrons are moved from a cathode electrode 18 to the light-emitting layer 15 through an electron transport layer 16 so that a light-emitting substance in the light-emitting layer is emitted to generate light by excitation of electrons due to the difference in energy levels in the light-emitting layer. Alternatively, an organic EL device can be fabricated by further comprising an electron transport layer 17 to increase electron formation efficiency. The organic EL device is formed of organic thin films consisting of organic compounds, such as the hole injection layer 13, hole transport layer 14, light-emitting layer 15, electron transport layer 16, and electron transport layer 17.

The driving principle of the organic EL device having the foregoing structure is as follows:

A hole injected from the anode extends to the light-emitting layer from the hole transport layer when a voltage is applied between the anode and cathode. On the other hand, electrons are injected from the cathode into the light-emitting layer via the electron transport layer so that carriers are bonded again in the light-emitting layer region to form an exciton. The exciton is changed from the excited state into the ground state. Accordingly, fluorescent molecules of the light-emitting layer are emitted to form an image.

On the other hand, Eastman Kodak developed an organic EL device using a low molecular aromatic diamine and aluminum complex as a light-emitting layer forming material for the first time in 1987 (Appl. Phys. Lett. 51, 913, 1987). Although compounds such as diphenylanthracene, tetraphenylbutadiene and distyrylbenzene derivatives have been developed as blue light-emitting substances, it is known that they tend to be easily crystallized because of their low thin film stability. Idemitsu Corporation developed a diphenyidistyryl based blue light-emitting substance in which branched phenyl groups hinder crystallization so that thin film stability is improved [H. Tikailin, H. Higashi, C. Hosogawa, EP 388,768 (1990)], and Kyushu University developed distyrylanthracene derivatives that improve thin film stability by having electron donor and acceptor [PRO. SPIE, 1910, 180 (1993)].

Furthermore, it is disclosed in Japanese Patent Laid-open Publication No. Heisei10-261488 that life cycle of the compound is extended by using distyrylanilin derivatives between 2.6 eV and 3.2 eV of electron affinity as blue light-emitting compounds, thereby improving thin film stability.

However, development of a new blue light-emitting compound must be immediately settled without delay to develop a blue light-emitting device or a full light-emitting device since these compounds have also low light-emitting efficiencies and are required to further improve thin film stability compared with other color light-emitting compounds.

SUMMARY OF THE INVENTION

In one embodiment, the present invention provides a blue light-emitting compound for organic EL devices represented by Chemical Formula 1:

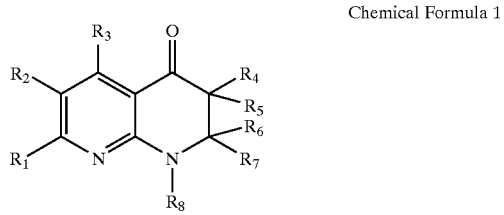

Chemical Formula 1 where R1 to R8 each independently represent a functional group selected from the group consisting of hydrogen, alkyl groups, alkoxy groups, carbon rings, aryl groups, hetero rings and fused aromatic compounds having from 1 to 30 carbon atoms; two of R1 to R3 may additionally be connected by a ring; and two of R4 to R8 may additionally be connected by a ring.

In another embodiment, the present invention provides an organic EL device comprising an organic film between a pair of electrodes, wherein the organic film comprises a compound represented by Chemical Formula 1:

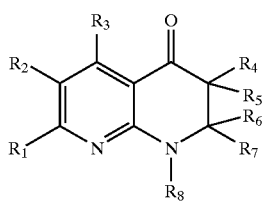

Chemical Formula 1 where R1 to R8 each independently represent a functional group selected from the group consisting of hydrogen, alkyl groups, alkoxy groups, carbon rings, aryl groups, hetero rings and fused aromatic compounds having from 1 to 30 carbon atoms; two of R1 to R3 may additionally be connected by a ring and two of R4 to R8 may additionally be connected by a ring.

BRIEF DESCRIPTION OF THE DRAWINGS

For a more complete understanding of the present invention and the advantages thereof, reference is now made to the following descriptions taken in conjunction with the accompanying drawings, in which like reference numerals denote like parts, wherein.

DETAILED DESCRIPTION OF PREFERRED EMBODIMENTS

Figure 1:
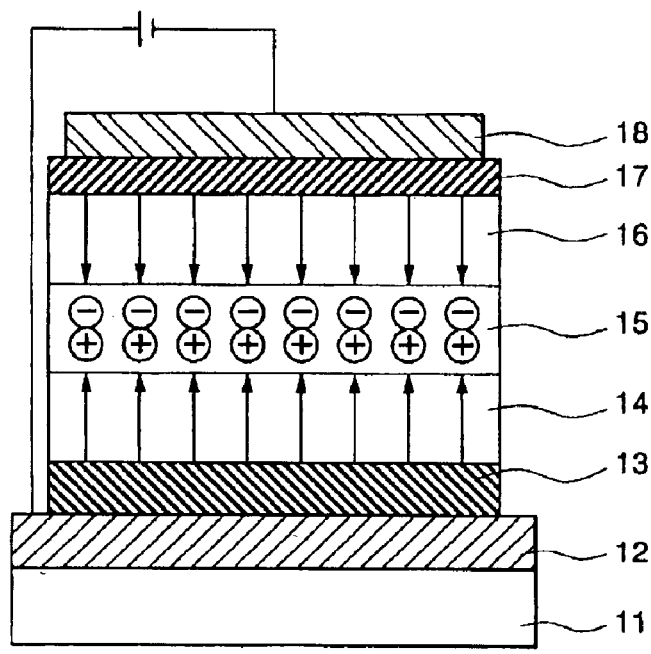
FIG. 1 is a cross-sectional view showing the structure of an organic EL device having the structure of substrate/anode/hole injection layer/hole transport layer/light-emitting layer/electron transport layer/electron injection layer/cathode.
Figure 2:
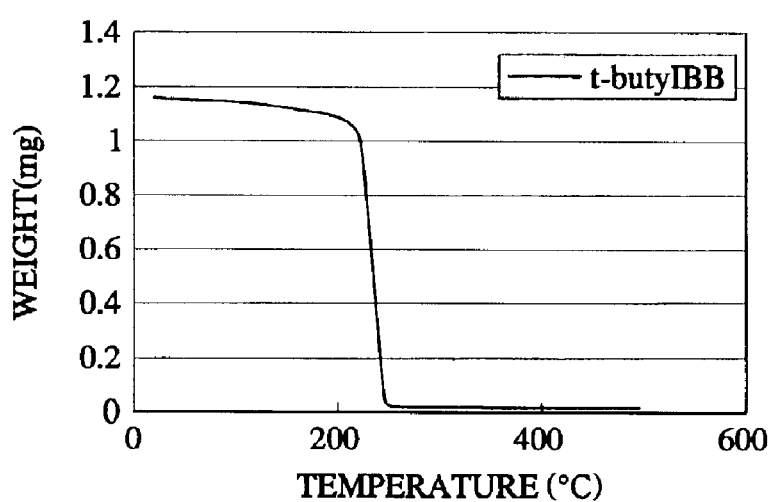
FIG. 2 illustrates a thermal decomposition curve of a material represented by Chemical Formula 2-e of the present invention.
Figure 3:
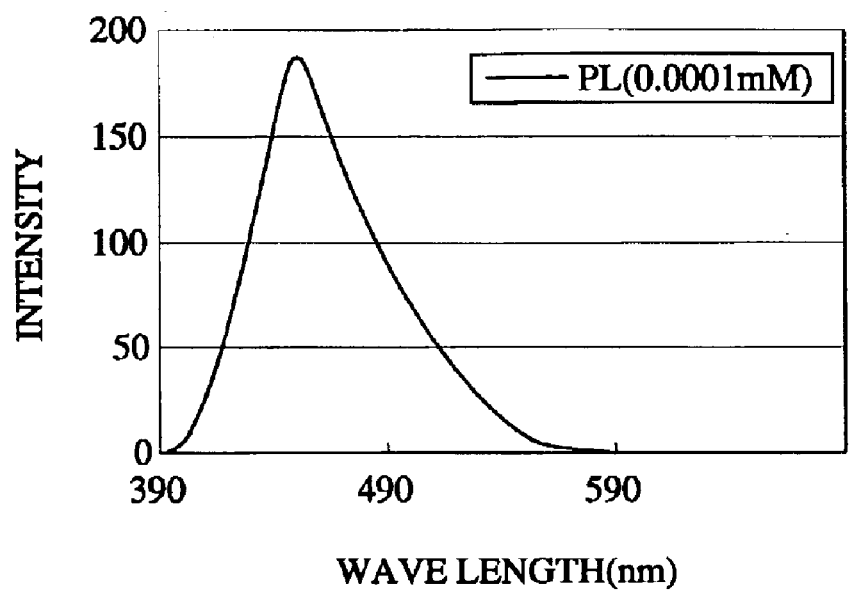
FIG. 3 is a drawing illustrating a photoluminescence (PL) spectrum of a compound represented by Chemical Formula 2-e of the present invention.
Figure 4:
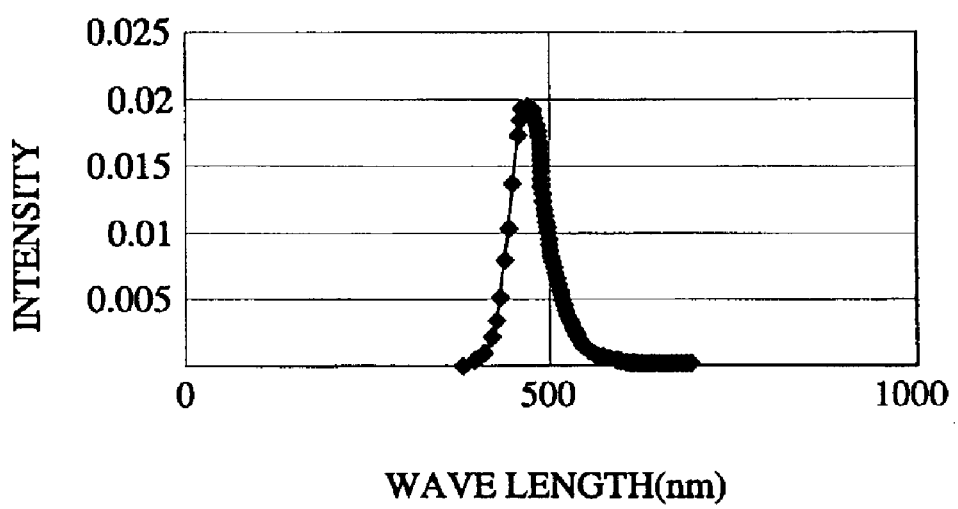
FIG. 4 is a drawing illustrating an EL spectrum when an organic EL compound represented by Chemical Formula 2-e of the present invention is introduced into a light-emitting layer.
Figure 5:
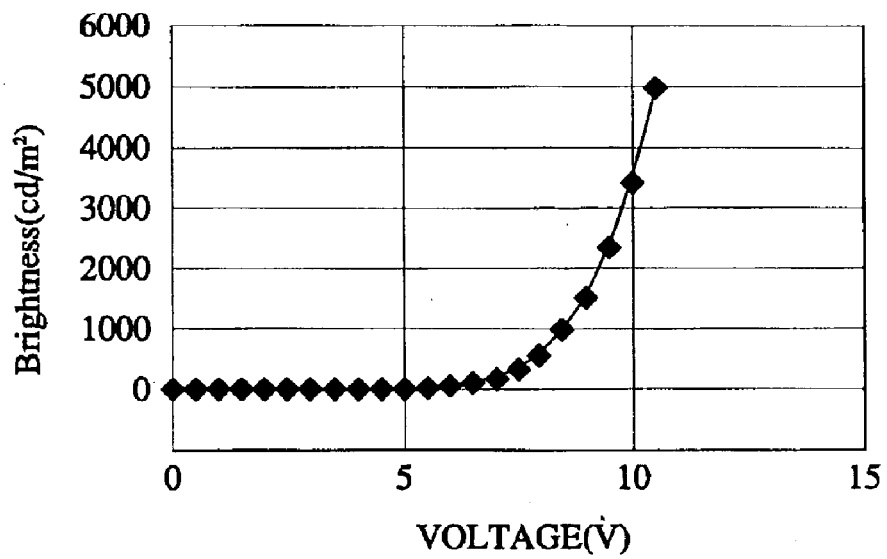
FIG. 5 is a drawing illustrating a VL spectrum when an organic EL compound represented by Chemical Formula 2-e of the present invention is introduced into a light-emitting layer.
Figure 6:
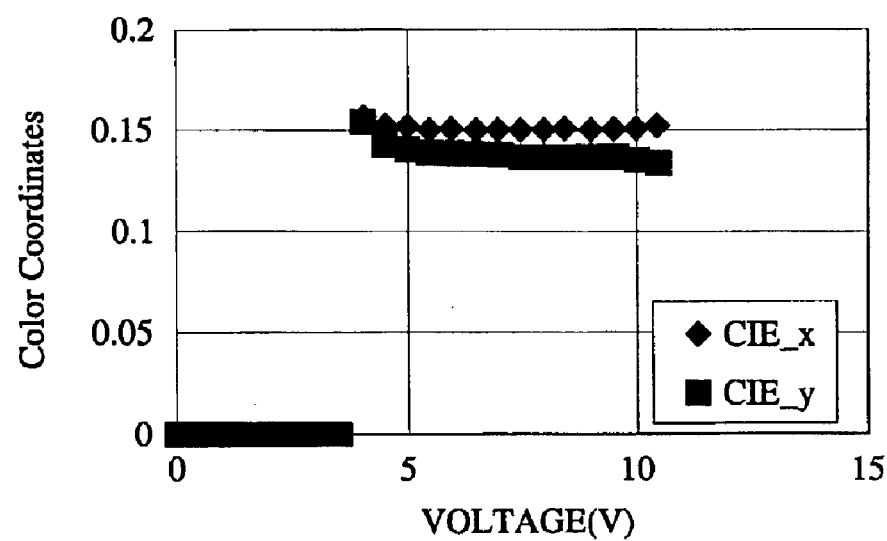
FIG. 6 is a drawing illustrating color coordinates when an organic EL compound represented by Chemical Formula 2-e of the present invention is introduced into a light-emitting layer.

Reference will now be made in detail to preferred embodiments of the present invention, examples of which are illustrated in the accompanying drawings.

The above Chemical Formula 1 has a very different structure compared to existing styryl based blue light-emitting substances because the structure of Chemical Formula 1 includes a pyridine group in the molecular structure. A compound of Chemical Formula 1 is capable of showing a blue single color light with stability because structurally an amine group is positioned at the ortho (o) position, and a carbonyl group is positioned at the meta (m) position. The reason why compounds of Chemical Formula 1 show potential to be stable compounds is that exciton reciprocal action is reduced by introducing a bulky structure so as to hinder π-stacking with an adjacent compound so that crystallization is suppressed, and thin film stability is increased as a result, thereby improving life cycle of the compound by positioning an electron-pair donor and an electron-pair acceptor in one molecule.

Furthermore, the compound of the Chemical Formula 1 has a high blue color purity and a high light-emitting efficiency due to the large energy gap because the number of double bonds is small between the electron donor and electron acceptor groups.

Furthermore, a blue light-emitting dopant compound used in the present invention has superior energy transfer due to the stereo-structure so that a high light-emitting efficiency is shown. In one embodiment, it is preferred that the R1 to R4 substituents in the above Chemical Formula 1 each independently represent a functional group selected from the group consisting of H, methyl groups, ethyl groups, propyl groups, n-butyl groups, I-propyl groups, t-butyl groups, sec-butyl groups, t-amyl groups, neopentyl groups, trifluoromethyl groups, pentafluoroethyl groups, perfluoroalkyl groups, heteroaryl groups, aryl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups.

Furthermore, preferably two of the R1, R2 and R3 groups are connected by a ring while two out of the R4 to R8 groups are connected by rings to each other.

A blue light-emitting compound of the present invention can be exemplified as follows in detail.

Compounds that are in the form of an alkyl group, alkoxy group, carbon ring, aryl group, hetero ring or fused aromatic compound having from 1 to 30 carbon atoms are as follows:

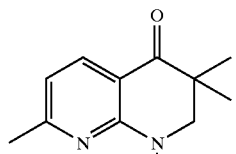

Chemical Formula 2-a

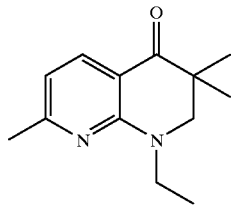

Chemical Formula 2-b

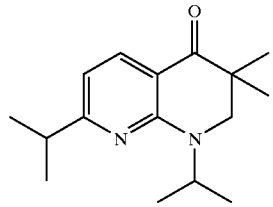

Chemical Formula 2-c

Chemical Formula 2-d
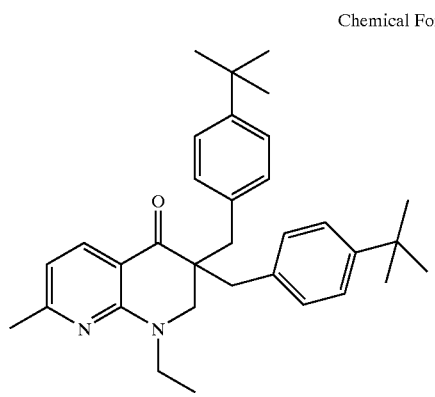
Chemical Formula 2-e
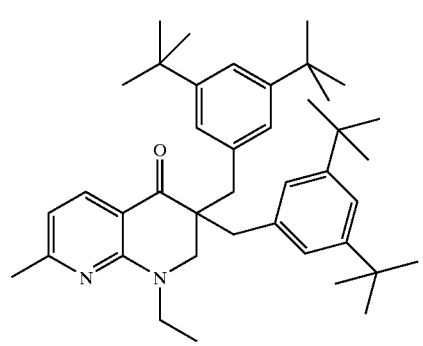
Chemical Formula 2-f
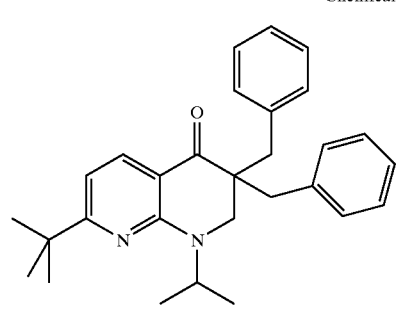
Chemical Formula 2-g
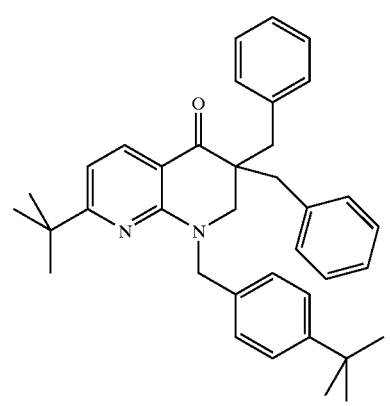
Chemical Formula 2-h
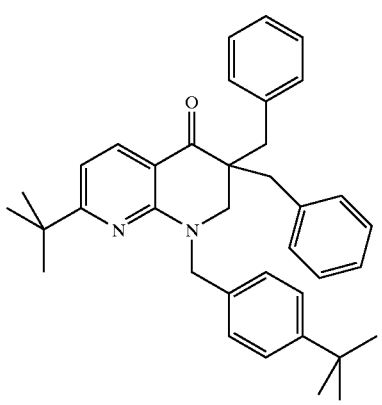
Chemical Formula 2-i
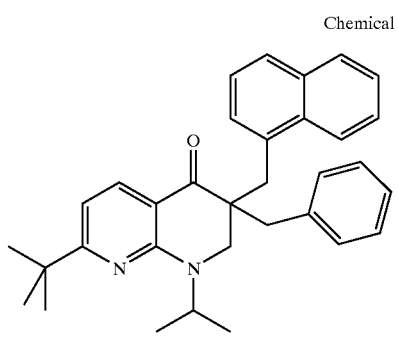
Chemical Formula 2-j
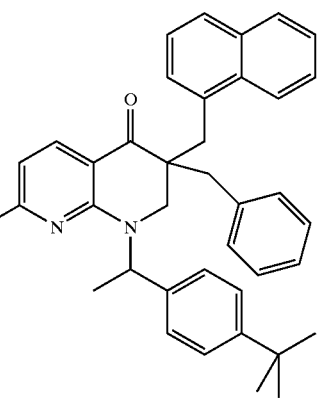
Chemical Formula 2-k
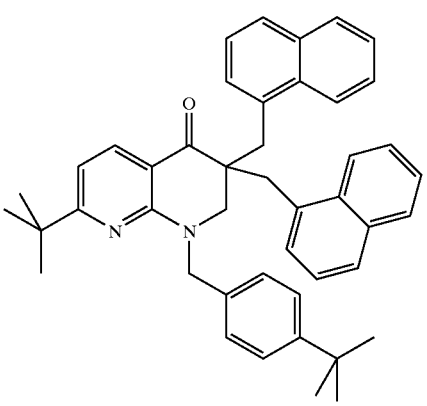

-continued

Chemical Formula 2-l

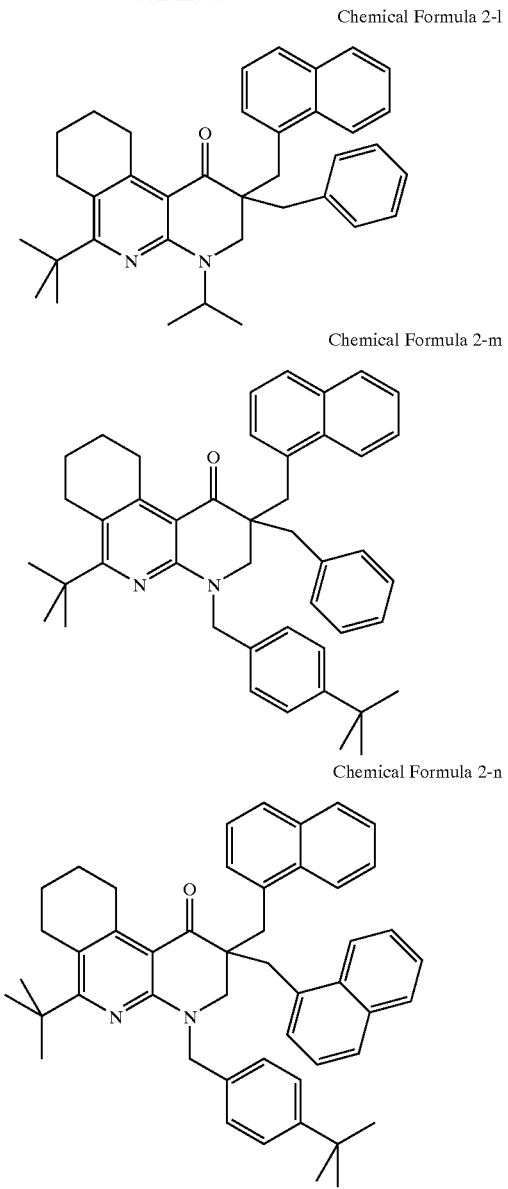

Chemical Formula 2-m

Chemical Formula 2-n

The structure of an organic EL device according to the present invention and a method for fabricating the organic EL device are explained below.

An organic EL device according to the present invention adopts the structure of an ordinary organic EL device, but it is different from the ordinary organic EL device, illustrated in FIG. 1, in that a material different from the ordinary material is used as a light-emitting substance of the light-emitting layer. Therefore, FIG. 1 is referred to so as to explain the structure of the organic EL device according to the present invention. In FIG. 1, the organic EL device according to the present invention comprises an organic film 15 between a cathode electrode 18 and an anode electrode 12.

The organic film 15 comprises an organic compound represented by Chemical Formula 1, and the organic film functions as a light-emitting layer or a dopant of the light-emitting layer.

Chemical Formula 1

In chemical Formula 1, R1 to R8 each independently represent a functional group selected from the group consisting of hydrogen, alkyl groups, alkoxy groups, carbon rings, aryl groups, hetero rings and fused aromatic compounds having from 1 to 30 carbon atoms; two of R1 to R3 may additionally be connected by a ring; and two of R4 to R8 may additionally be connected by a ring.

More preferably, R1 to R4 each independently represents a functional group selected from the group consisting of H, methyl groups, ethyl groups, propyl groups, n-butyl groups, I-propyl groups, t-butyl groups, sec-butyl groups, t-amyl groups, neopentyl groups, trifluoromethyl groups, pentafluoroethyl groups, perfluoroalkyl groups, heteroaryl groups, aryl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups.

Furthermore, preferably two out of the R1, R2 and R3 groups are connected by a ring while two out of three of the R4 to R8 groups are connected by rings to each other.

An organic EL device according to one embodiment of the present invention further comprises a hole injection layer 12 and/or a hole transport layer 14 between the organic film 15 and the anode electrode 12. A typically used material, such as starburst-type diphenylamine, PEDOT or PANI, can be used for the hole injection layer and/or hole transport layer. The organic EL device according to one embodiment of the present invention further comprises an electron transport layer 16 and/or an electron injection layer 17 between the organic film 15 and the cathode electrode 18. Typically used materials are also used for the electron transport layer and the electron injection layer.

A method for fabricating an organic EL device according to one embodiment of the present invention is as follows.

First, an anode electrode is formed by coating a material for the anode electrode on the upper part of a substrate, wherein a substrate typically used in an organic EL device is used as the substrate. More preferably, the substrate is a glass substrate or a transparent plastic substrate having superior transparency, surface flatness, handling easiness and waterproofness.

Preferably indium tin oxide (ITO), tin oxide ($SnO_2$) or zinc oxide (ZnO), which are transparent and have superior conductivities, is used as the material for the anode electrode.

A hole injection layer material is vacuum-deposited or spin-coated on the upper part of the anode electrode. The hole injection layer material is not particularly restricted. However, CuPc or IDE406 is preferably used as the hole injection layer material.

Subsequently, a hole transport layer material is vacuum-deposited or spin-coated on the upper part of the hole injection layer. Although the hole transport layer material is not particularly limited, it is preferred to use N,N'-bis(3-methylphenyl)-N,N'-diphenyl-[1,1-biphenyl]-4,4'-diamine (TPD), N,N'-di(naphthalene-1-il)-N,N'-diphenylbenzidine, N,N'-di(naphthalene-1-il)-N,N'-diphenyl-benzidine (α-NPD), or the like as the hole transport layer material.

A light-emitting layer is introduced onto the upper part of the hole transport layer, and a material of the chemical formula 1 according to the present invention can be used as a host substance of the light-emitting layer. As the host substance of the light-emitting layer, an ordinary light-emitting layer forming material such as IDE120 and a material of Chemical Formula 1 according to the present invention can be jointly deposited as a dopant.

The doping concentration is not particularly limited when the material of the Chemical Formula 1 is used as a dopant. Deposition techniques include ink jet printing and laser induced thermal imaging.

An electron transport layer is vacuum-deposited or spin-coated as a thin film on the light-emitting layer. It is preferred to use Alq3 as an electron transport layer material.

Furthermore, an electron injection layer can be further deposited on the upper part of the electron transport layer. Materials such as LiF, NaCl, CsF, and the like can be used as the electron injection layer.

Subsequently, an organic EL device is completed by vacuum-depositing a cathode forming metal on the upper part of the electron injection layer, thereby forming a cathode electrode when an electron transport layer or an electron injection layer is introduced.

The cathode forming metal preferably comprises Li, Mg, Al, Al—Li, Ca, Mg—In, or Mg—Ag.

One organic layer or two intermediate layers can be additionally formed on an organic EL device of the present invention by adding an organic layer or intermediate layers to the structure of the anode electrode, hole injection layer, hole transport layer, light-emitting layer, electron transport layer, electron injection layer, and/or cathode electrode depending on the application.

Preferred examples of the present invention are as follows. The following examples are provided only for a better understanding of the present invention. However, the present invention is not limited to the following examples.

Reagents to be Used

Nalidixicaacid, borane dimethyl sulfide complex, tetrahydrofuran (THF) and 4-(t-butyl) benzyl bromide manufactured by Aldrich Corporation were used, and lithium diisopropyl amide (LDA) manufactured by ACROS Corporation was used. The refined tetrahydrofuran (THF) was used after refining THF by a method disclosed in the literature. Methylenechloride, ethylacetate, ammoniumchloride, hexane, acetone, magnesium sulfide, and sodium bicarbonate, etc manufactured by Duksan Chemical Co., Ltd. were used.

General Method $^1$H-NMR, $^{13}$C-NMR, UV and spectrofluorometer were used to confirm structures of all new compounds. The $^1$H-NMR and $^{13}$C-NMR were recorded using a spectroscope, the UV was recorded using a BECKMAN DU-650 instrument, and the spectrofluorometer was recorded using a JASCO FP-750 instrument. All chemical mobility was recorded as parts per million on the basis of solvent.

SYNTHESIS EXAMPLES

Compound Synthesis of Chemical Formula 2-e in One Example of The Present Invention Synthesis 1

Method for preparing a material of Chemical Formula 4 (R1=Me, R2=Ethyl, R3=H, and R4=H) (Chemical Reaction Formula 1)

12.5 mmol of a material of Chemical Formula 3 and 26.12 mmol of borane dimethyl sulfide complex were introduced into 10 ml of tetrahydrofuran at 0° C., and the mixture was agitated under nitrogen at a temperature of 70° C. for 10 hours by putting. An extract was extracted with methylenechloride after checking the reaction using TLC and quenching the reacted material using 5 ml of methanol and 10 ml of H$_2$O. The extracted methylenechloride layer was washed with a saturated Na$_2$CO$_3$ aqueous solution. The solvent was removed from the water-removed solution by reduced pressure distillation after removing water from the extracted methylenechloride solution using a MgSO$_4$ drying agent. A compound of Chemical Formula 4 having a yellow color was obtained by separating the concentrated solution using column chromatography. Yield was 45%.

1H-NMR (CDCl$_3$, 300 MHz): δ(ppm) 1.07(t, J=7.1 Hz, 3H), 2.30(S, 3H), 2.559(t, J=7.3 Hz, 2H), 3.40(t, J=7.1 Hz, 2H), 3.659(q, J=7.0 Hz, 2H), 6.36(d, J=7.0 Hz, 1H), 7.82(d, J=7.7 Hz, 1H).

Chemical Formula 3

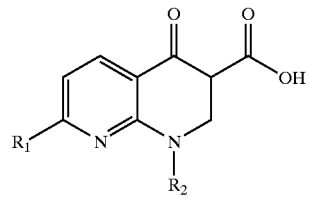

Chemical Formula 4

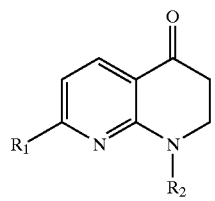

Chemical Reaction Formula 1

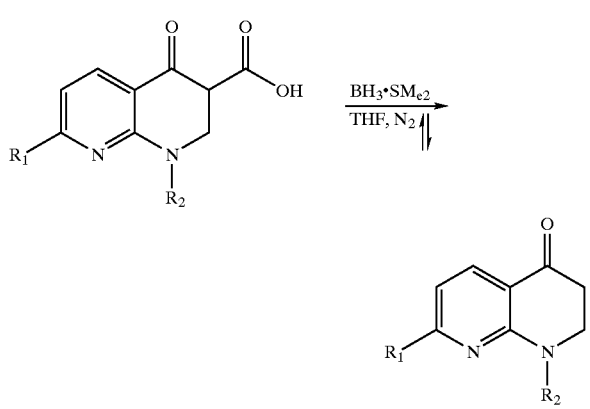

Synthesis 2

Method for preparing a material of Chemical Formula 2-e (R1=Me, R2=ethyl, R3=4-(tert-butyl) benzyl (Chemical Reaction Formula 2)

10 ml of tetrahydrofuran were introduced into 5.25 mmol of a material of Chemical Formula 4 under nitrogen at room temperature, and a yellow solution was obtained by agitating the mixture for about 30 minutes. The mixture was agitated at a temperature of −78° C. for 1 hour while slowly putting 6.24 mmol of lithium diisopropyl amide into the solution. The resulting solution was slowly introduced into 0.97 mmol of 4-(t-butyl) benzylbromide prepared by agitating the materials for about 30 minutes in advance after adding 10 ml of tetrahydrofuran. The reaction of the agitated material was checked by TLC after agitating the mixed solution for 8 hours. An extract was extracted with methylenechloride after quenching the reacted material using 5 ml of ammonium chloride solution. The extracted methylenechloride layer was washed with a saturated $Na_2CO_3$ aqueous solution. The solvent was removed from the water-removed solution by reduced pressure distillation after removing water from the extracted methylenechloride solution using a $MgSO_4$ drying agent. A whitish yellowish solid was obtained by separating the concentrated solution using column chromatography, and a blue fluorescent light-emitting compound of Chemical Formula 2-e was obtained by drying the solid under vacuum pump for 3 hours. Yield was 96%.

1H-NMR ($CDCl_3$, 300 MHz): δ(ppm) 1.14(t, J=7.0 Hz, 3H), 2.44(S, 3H), 2.61–3.24(D of D, J=13.5 Hz, 4H), 3.14(s, 2H), 3.84(q, J=6.8 Hz, 2H), 6.52(d, J=7.8 Hz, 1H), 7.10(t, J=8.2 Hz, 4H), 7.28(t, J=2.2 Hz), 8.09(d, J=7.8 Hz, 1H).

Chemical Reaction Formula 2

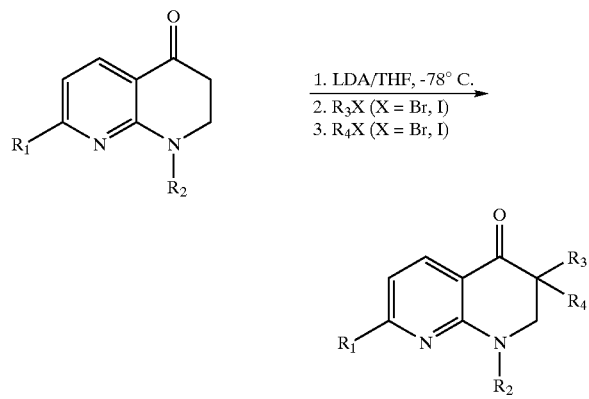

Fabrication of an Organic EL Device

EXAMPLE

A hole injection layer having a thickness of 600 Å was formed by using a 10 Ω/cm² ITO substrate as an anode and vacuum depositing IDE406 on the upper part of the substrate. Subsequently, a hole transport layer was formed by vacuum-depositing a compound of the following Chemical Formula 5 on the upper part of the hole injection layer at a thickness of 200 Å. A light-emitting layer having a thickness of 180 Å was formed by forming a compound of the Chemical Formula 2-e, 10% of which was doped with a host substance of IDE120, on the upper part of the hole transport layer. An electron transport layer having a thickness of 250 Å was formed by vacuum depositing a compound of the following Chemical Formula 6 on the upper part of the light-emitting layer. An organic EL device was fabricated as illustrated in FIG. 1 by sequentially vacuum-depositing 10 Å of LiF and 3000 Å of Al on the electron transport layer, thereby forming LiF/Al electrodes.

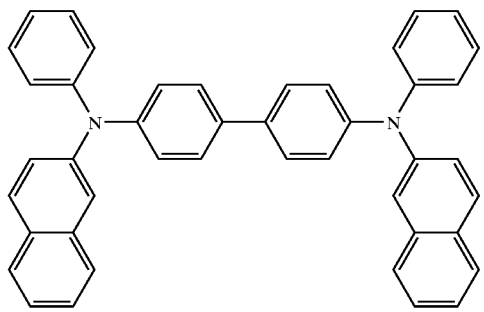

Chemical Formula 5

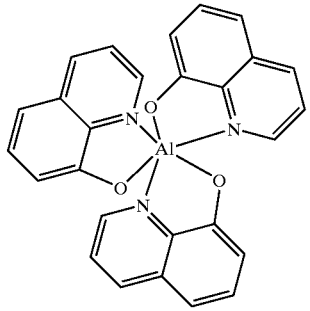

Chemical Formula 6

Comparative Example

An organic EL device was fabricated using the same method as in the EXAMPLE by using an existing IDE120 compound instead of a compound of Chemical Formula 2-e as the light-emitting layer. Color characteristics of the organic EL device fabricated according to the EXAMPLE and COMPARATIVE EXAMPLE were examined, and the results are set forth in the following Table 1.

TABLE 1

|  | Color coordinates | Efficiency |
|---|---|---|
| EXAMPLE | (0.15, 0.14) | 4 cd/A |
| COMPARATIVE EXAMPLE | (0.15, 0.15) | 2.5 cd/A |

As shown in the above Table 1, an organic EL device of the EXAMPLE could realize blue color having superior color purity compared to the organic EL device of the COMPARATIVE EXAMPLE, and the former also shows excellent performance of light-emitting efficiency compared to the latter. An organic EL device of a blue light-emitting compound according to the EXAMPLE has a maximum wavelength of 452 nm, and thus shows superior color purity.

As described above, a compound of Chemical Formula 1 according to the present invention as a blue light-emitting substance has superior color purity and is useful as a coloring material for display devices. Furthermore, an organic EL device according to the present invention forms an organic film such as a light-emitting layer by using a compound of Chemical Formula 1, and has improved thin film stability and luminance characteristics compared to an organic EL device using an ordinary blue light-emitting compound.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A blue light-emitting compound for an organic EL device represented by Chemical Formula 1:

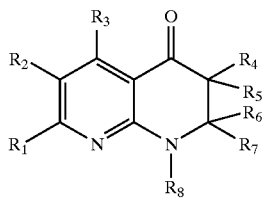

Chemical Formula 1 wherein R1 is selected from the group consisting of, ethyl groups, propyl groups, n-butyl groups, i-propyl groups, t-butyl groups, sec-butyl groups, t-amyl groups, neopentyl groups, trifluoromethyl groups, pentafluoroethyl groups, perfluoroalkyl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups, R2 to R8 each independently represents H or a substituted or unsubstituted functional group with up to 30 carbons selected from the group consisting of alkyl groups, alkoxy groups, carbon rings, aryl groups, heteroaryl groups, hetero rings and fused aromatic compounds; wherein two of R1, R2 and R3 may be connected by a ring; and wherein two of R4 to R8 may be connected by a ring.

2. A blue light-emitting compound for an organic EL device represented by Chemical Formula 1:

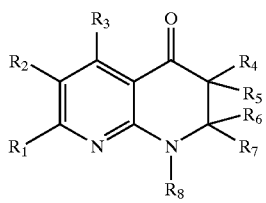

Chemical Formula 1 wherein R1 represents a functional group selected from the group consisting of ethyl groups, propyl groups, n-butyl groups, i-propyl groups, t-butyl groups, sec-butyl groups, t-amyl groups, neopentyl groups, trifluoromethyl groups, pentafluoroethyl groups, perfluoroalkyl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups, R2 to R4 each independently represents a functional group selected from the group consisting of H, ethyl groups, propyl groups, n-butyl groups, i-propyl groups, t-butyl groups, sec-butyl groups, t-amyl groups, neopentyl groups, trifluoromethyl groups, pentafluoroethyl groups, perfluoroalkyl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups and R5 to R8 each independently represents H or a substituted or unsubstituted functional group with up to 30 carbons selected from the group consisting of alkyl groups, alkoxy groups, carbon rings, aryl groups, heteroaryl groups, hetero rings and fused aromatic compounds.

3. A blue light-emitting compound for an organic EL device, wherein the compound is a compound selected from the group consisting of the compounds of Chemical Formulae 2-a to 2-n:

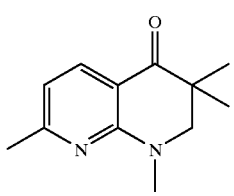

Chemical Formula 2-a

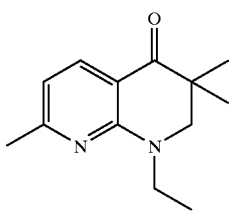

Chemical Formula 2-b

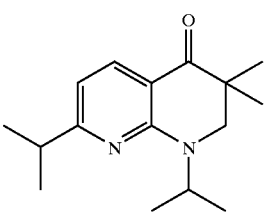

Chemical Formula 2-c

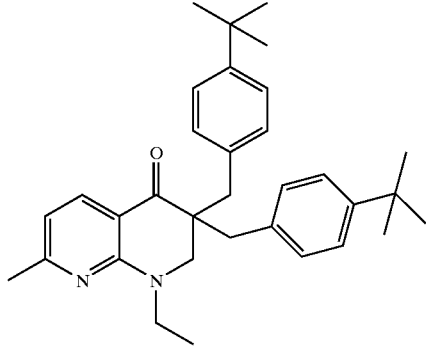

Chemical Formula 2-d

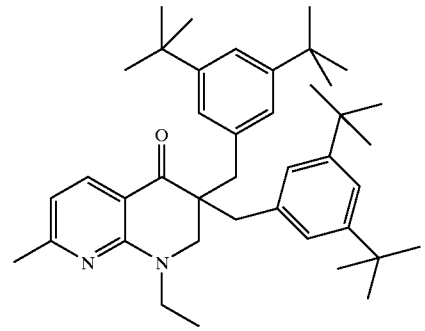

Chemical Formula 2-e

Chemical Formula 2-f
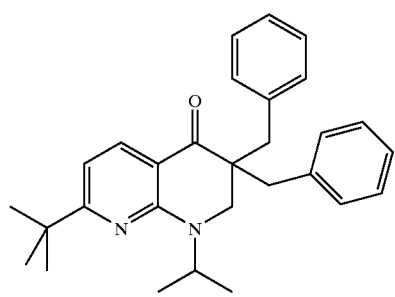
Chemical Formula 2-g
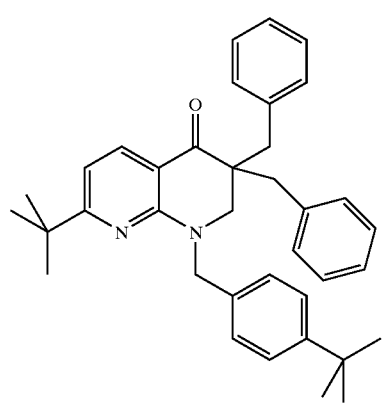
Chemical Formula 2-h
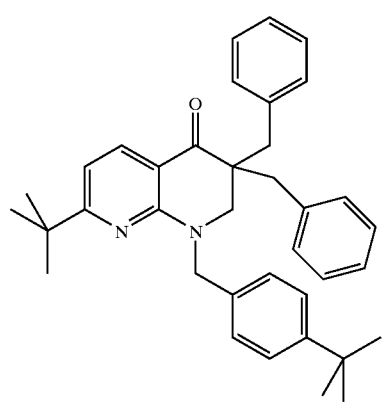
Chemical Formula 2-i
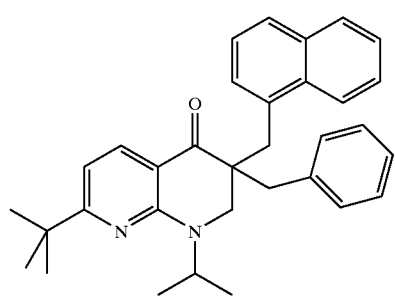
Chemical Formula 2-j
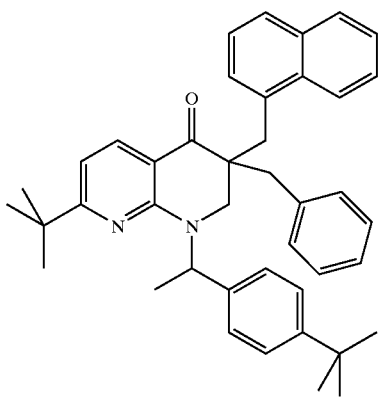
Chemical Formula 2-k
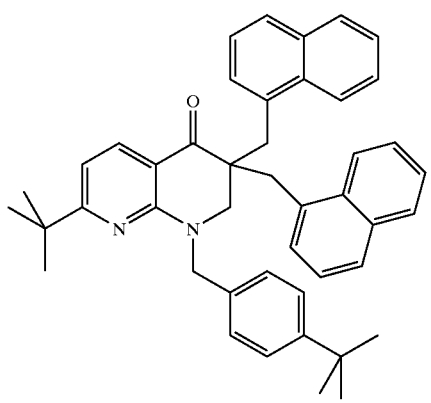
Chemical Formula 2-l
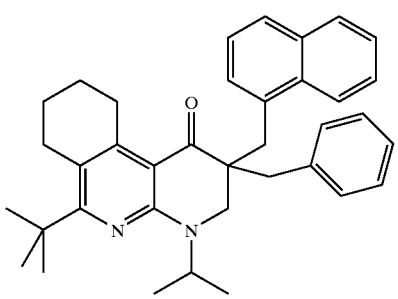
Chemical Formula 2-m
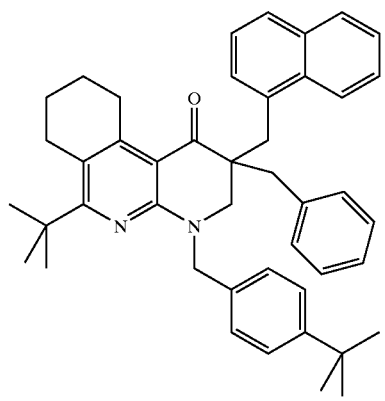
and Chemical Formula 2-n

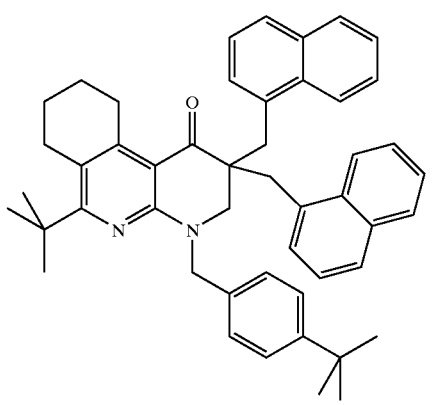

Chemical Formula 2-a

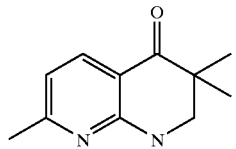

Chemical Formula 2-b

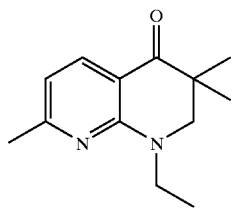

Chemical Formula 2-c

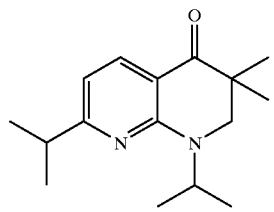

Chemical Formula 2-d

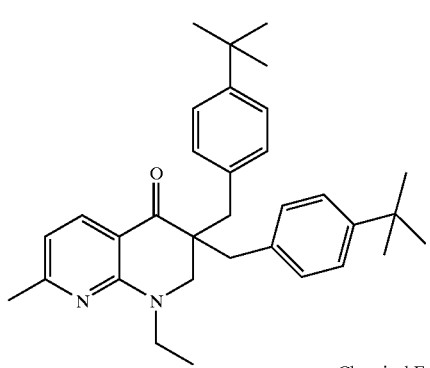

Chemical Formula 2-e

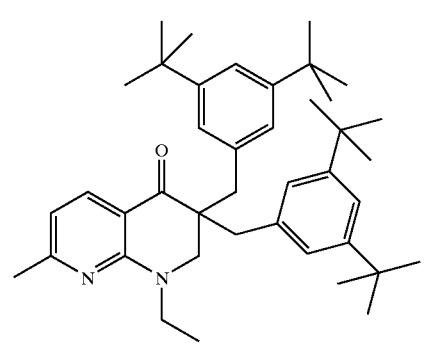

Chemical Formula 2-f

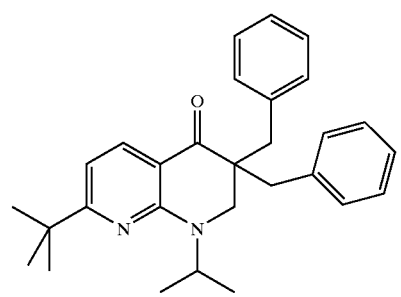

4. An organic EL device comprising an organic film between a pair of electrodes, wherein the organic film comprises a compound represented by Chemical Formula 1:

Chemical Formula 1

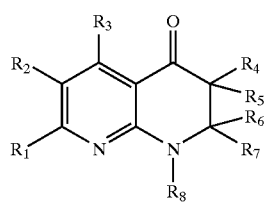

wherein R1 to R8 each independently represents H or a substituted or unsubstituted functional group with up to 30 carbons selected from the group consisting of alkyl groups, alkoxy groups, carbon rings, heteroaryl groups, aryl groups, hetero rings and fused aromatic compounds; wherein two of R1, R2 and R3 may be connected by a ring; and wherein two of R4 to R8 may be connected by a ring.

5. The organic EL device according to claim 4, wherein the organic film is a light-emitting layer.

6. The organic EL device according to claim 5, wherein the organic EL device further comprises a hole transport layer between an anode electrode and the organic film.

7. The organic EL device according to claim 5, wherein the organic EL device further comprises an electron injection layer between a cathode electrode and the organic film.

8. The organic EL device according to claim 4, wherein the compound of Chemical Formula I is a dopant of the organic film which functions as a light emitting layer.

9. The organic EL device according to claim 4, wherein R1 to R4 each independently represents a functional group selected from the group consisting of H, methyl groups, ethyl groups, propyl groups, n-butyl groups, i-propyl groups, t-butyl groups, sec-butyl groups, t-amyl groups, neopentyl groups, trifluoromethyl groups, pentafluoroethyl groups, perfluoroalkyl groups, benzyl groups, 4-(t-butyl) benzyl groups, 3,5-di-(t-butyl) benzyl groups, 3,5-di-(isopropyl) benzyl groups, naphthyl groups, phenyl groups, thienyl groups and pyridyl groups.

10. An organic EL device comprising an organic film between a pair of electrodes, wherein the organic film comprises a compound selected from the group consisting of compounds of Chemical Formulae 2-a to 2-n:

Chemical Formula 2-g
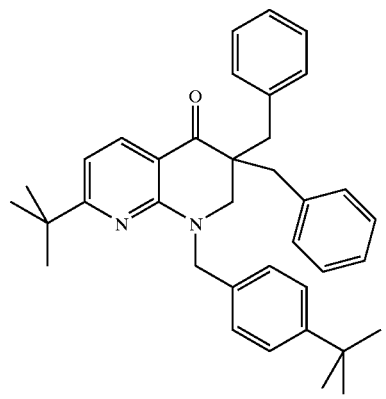
Chemical Formula 2-h
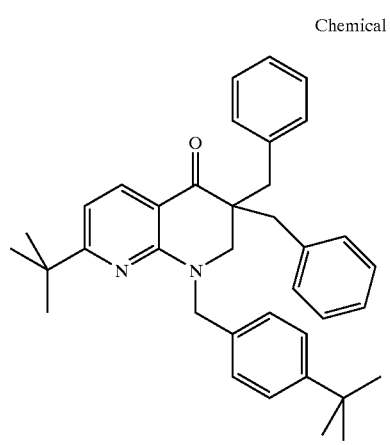
Chemical Formula 2-i
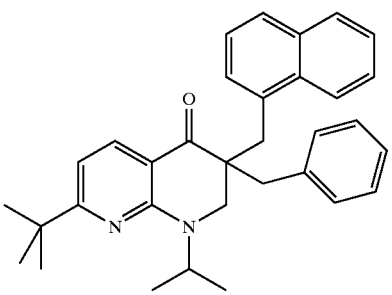
Chemical Formula 2-j
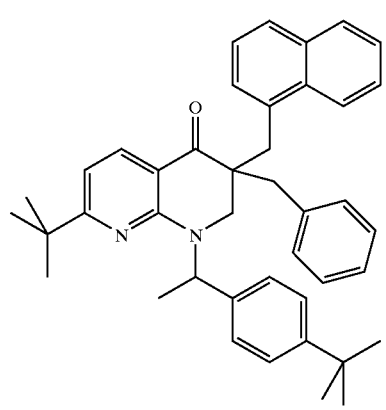
Chemical Formula 2-k
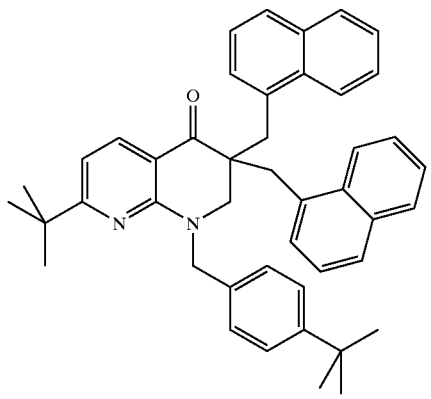
Chemical Formula 2-l
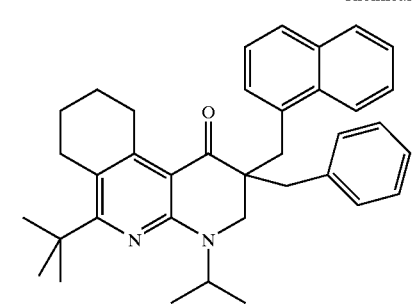
Chemical Formula 2-m
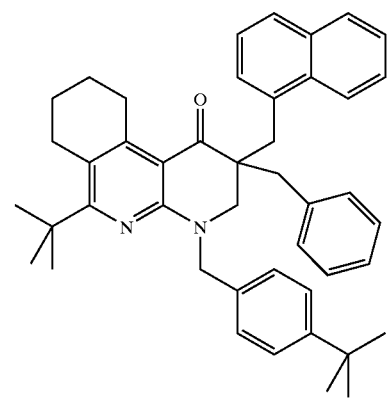
and
Chemical Formula 2-n
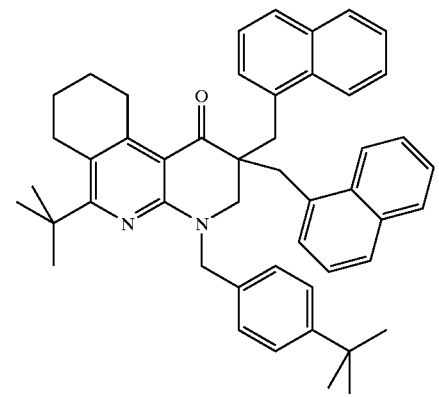
* * * * *